United States Patent
Visness et al.

(10) Patent No.: US 6,494,854 B1
(45) Date of Patent: Dec. 17, 2002

(54) CERVICAL COLLAR DEVICE

(75) Inventors: Joel K. Visness, Rosemount, MN (US); Eric F. Caille, Richfield, MN (US)

(73) Assignee: PMT Corporation, Chanhassen, MN (US)

( * ) Notice: Subject to any disclaimer, the term of this patent is extended or adjusted under 35 U.S.C. 154(b) by 66 days.

(21) Appl. No.: 09/696,214

(22) Filed: Oct. 25, 2000

Related U.S. Application Data
(60) Provisional application No. 60/162,187, filed on Oct. 28, 1999.

(51) Int. Cl.$^7$ .................................................. A61F 5/00
(52) U.S. Cl. .................................. 602/18; 128/DIG. 23
(58) Field of Search ............................. 602/5, 17, 18; 128/DIG. 23

(56) References Cited

U.S. PATENT DOCUMENTS

| | | | |
|---|---|---|---|
| 4,538,597 A | * 9/1985 | Lerman | 602/18 |
| RE32,219 E | 8/1986 | Garth | |
| 4,745,922 A | * 5/1988 | Taylor | 602/18 |
| 5,058,572 A | * 10/1991 | Schmid | 602/18 |
| 5,097,824 A | 3/1992 | Garth | |
| 5,180,361 A | 1/1993 | Moore et al. | |
| 5,437,612 A | 8/1995 | Moore et al. | |
| 5,593,382 A | * 1/1997 | Rudy | 602/18 |
| 5,797,713 A | * 8/1998 | Tweardy | 602/18 |

\* cited by examiner

*Primary Examiner*—Michael A. Brown
(74) *Attorney, Agent, or Firm*—Anthony G. Eggink (57) ABSTRACT

A cervical collar assembly to immobilize the neck and head of a user. The assembly includes an adjustable and conformable shell member having a pad member secured on its interior to engage the skin of the user. The shell member is comprised of a front member, a back member and means to adjustable join the front and back members. A chin support member is adjustably secured to the front member and an occipital support member is secured to the back member. The front and back members are provided with a plurality of elongated slits which permit the shell member to conform to the neck and head areas of the user. Further, the front member is provided with opposing upwardly extending tab members to engage the mandibula of a user's jaw to aid in the immobilization of the neck and head of the user.

26 Claims, 6 Drawing Sheets

CERVICAL COLLAR DEVICE

This application claims the benefit of U.S. Provisional Application No. 60/162,187 filed on Oct. 28, 1999.

BACKGROUND OF THE INVENTION

This invention relates generally to a cervical collar device to partially immobilize the head and neck of a patient while allowing comfortable extended wear. More particularly, this invention relates to an improved cervical collar assembly which allows comfortable extended wear while partially immobilizing the head and neck of a patient.

SUMMARY OF THE INVENTION

The cervical collar device or assembly is constructed and arranged to limit movement of the neck and head to treat neck pain and/or instability due to injury. The cervical collar device supports parts of the head and holds the head and neck in a fixed position by limiting flexion, extension, rotation and lateral movement of the head.

The cervical collar is formed of a stiff, semi-rigid plastic material comprising a front and back portion to form a shell collar structure. The front and back portions are joined and secured by hook and loop fasteners. The front portion provides an adjustable chin support that allows the flexion angle to be adjusted to fit a variety of patients or to meet a physician's requirements. The front portion has side mandible controls included on the main body of the front portion to reduce lateral movement of the patient's head.

Prior art cervical collar devices have relied primarily on chin support structures to control lateral movement of the head. However, the mandible controls of the present invention aid in reducing the feeling of the chin being constricted or giving the user a trapped feeling when wearing the cervical collar device of the invention. The back portion of the shell structure is of a two piece construction which provides an occipital support, which supports and contours to the patient's head and neck, and which is attached to the main body of the back portion. The occipital support is constructed of a rigid plastic material and has a predetermined shape which mimics a human hand holding the back of the head using the thumb and forefinger. For example, the occipital support may have a "T" or triangular shape. The upper portion of the back piece "cradles" the occipital region, restricting movement in all three planes. The occipital support is designed to equally distribute the weight of the head thereon. The shell structure of the collar device also has the slot patterns in both the front and back portions. These slots provide a device which allows greater conformity to the patient's head and neck. These slots also reduce weight and provide air circulation through the device to produce a more breathable collar for extended wear.

The cervical collar device has a structural configuration to disperse and cushion the weight of the device and the resultant head and neck forces of the patient on the device. It has been found that a concentrated pressure over time to the patient's body can result in skin breakdown, i.e., ulcerated skin. Thus, the bottoms of the front and back portions of the shell structure have a generally flat and rounded configuration to spread the weight across the sternum or chest areas. Further, edges of specified areas of the front and back portions may be provided with soft gasket members to further cushion the device against the patient's body. The structural configuration of the cervical collar device has a structure to provide a stable device which minimizes pressure points and which is provided with cushioned gasket members.

The collar device is anatomically designed in multiple sizes to accommodate the physiology of various neck and head configurations and sizes. An object of the present invention is to provide a cervical collar assembly that provides conforming support to the head and neck while also providing patient comfort over extended periods of time.

In summary, the invention provides an adjustable structure having a "hook and catch" chin support system, an occipital support system that contours to the natural shape of the patient's head, slots and slot patterns allowing for a more adjustable and breathable collar, and mandible control tabs to restrict lateral and rotational movement of a patient's head.

These and other benefits of this invention will become clear from the following description by reference to the drawings.

DESCRIPTION OF THE PREFERRED EMBODIMENTS

Figure 1:
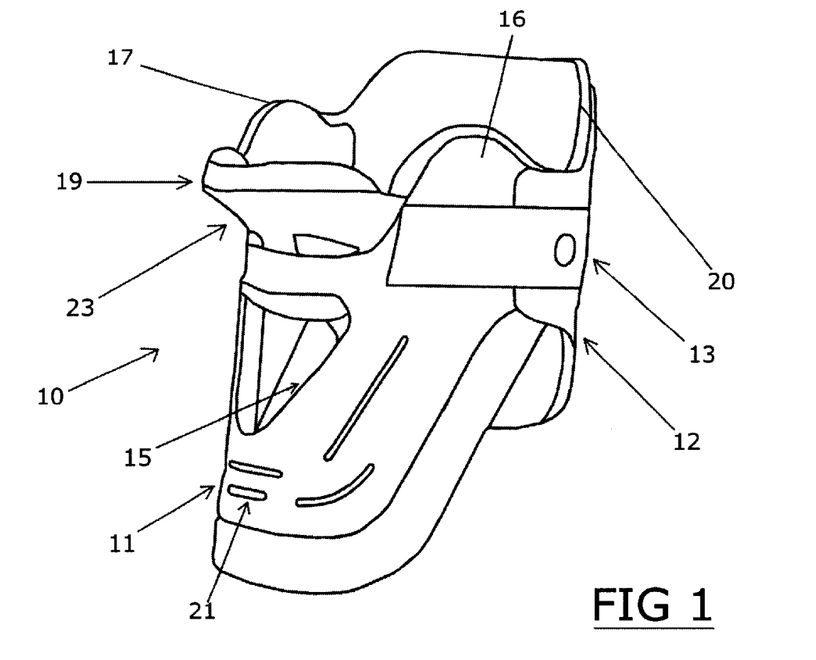
FIG. 1 is a perspective view of the cervical collar assembly of the present invention.
Figure 2:
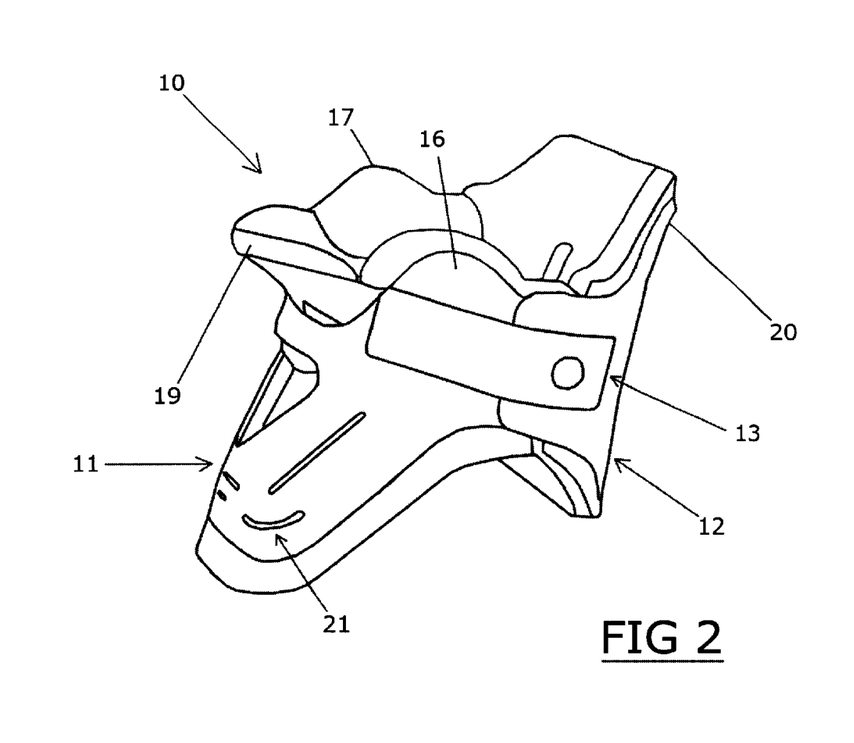
FIG. 2 is another perspective view of the cervical collar assembly and showing the front and back portions of the assembly of FIG. 1.

Referring to FIGS. 1 and 2 the cervical collar assembly 10 is shown and which is provided to partially immobilize the head and neck of a patient while allowing comfortable extended wear for the patient or user. The cervical collar device 10 is constructed and arranged to limit movement of the neck and head to treat neck pain and/or instability due to injury. The cervical collar device 10 supports parts of the head and holds the head and neck in a fixed position by limiting flexion, extension, rotation and lateral movement of a user's head.

The objective of the present invention is to provide a cervical collar assembly 10 that provides superior support to the head and neck while also providing patient comfort over extended periods of time. The cervical collar device 10 is anatomically designed in multiple sizes, i.e., infant, small, medium and large to accommodate the physiology of various neck and head configurations and sizes.

Referring to FIGS. 1 and 2, the cervical collar assembly 10 is shown comprising a front portion 11 and back portion 12 which form a shell member. The front and back portions 11 and 12 are joined and secured by hook and loop fastener members 13 and 14. The front and back portions 11 and 12 are preferably formed of stiff, semi-rigid plastic structure that may be flexed, as will be further described. The front portion 11 further may have an adjustable chin support 23 that allows the flexion angle to be adjusted to fit a variety of patients or to meet a physician's requirements. The front portion 11 is shown to have side mandible control tabs 16 and 17 extending from the main body of the front portion 11. The mandible control tabs 16 and 17 are provided to reduce lateral movement of a patient's head. The front member 11 is also shown to have an enlarged opening 15 for the trachea.

Figure 3:
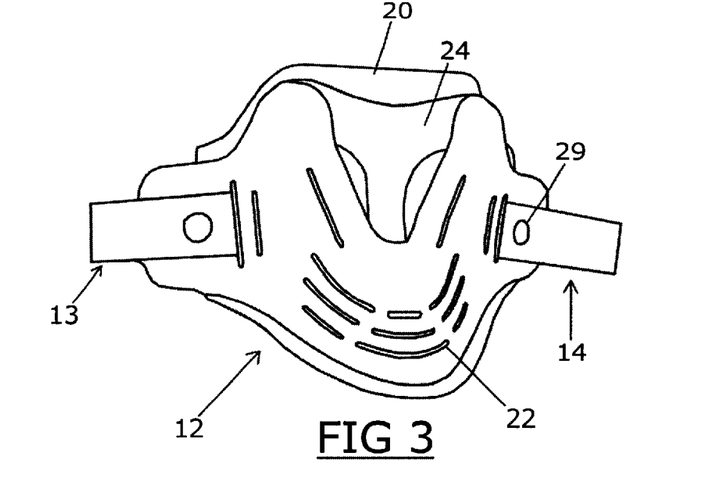
FIG. 3 is a plan view of the back portion of the cervical collar assembly of FIGS. 1 and 2.
Figure 8:
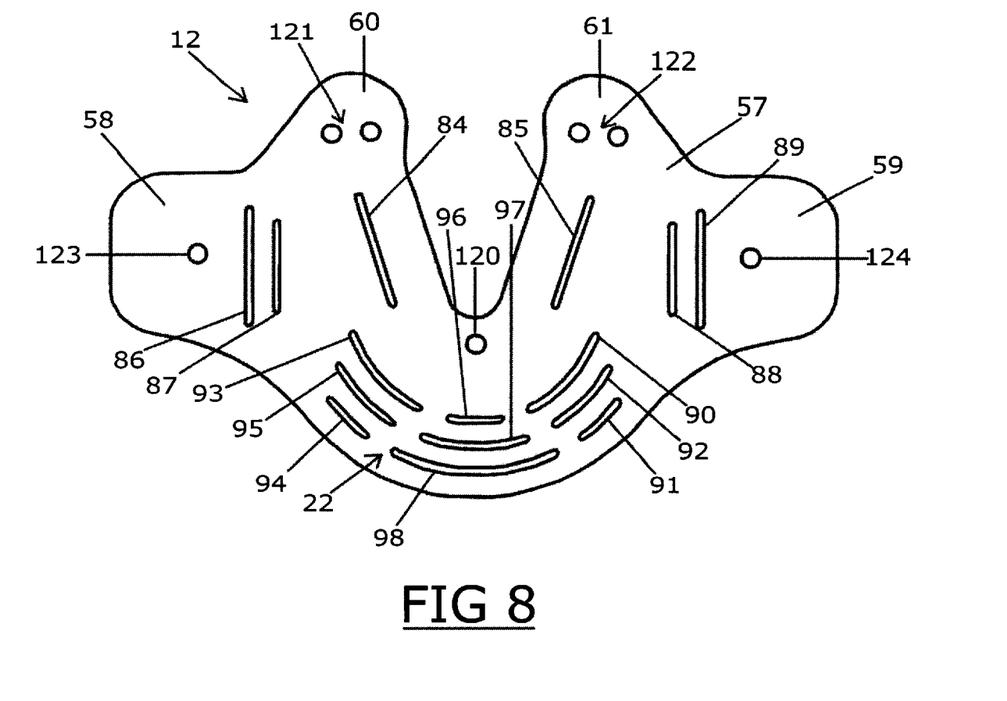
FIG. 8 is a plan view of the back portion of the cervical collar assembly of FIG. 1.

The front and back portions 11 and 12 are preferably formed of a stiff, flexible, molded plastic material which is MRI and biocompatible. The fastener members 13 and 14 and other elements of the collar assembly, are preferably constructed of a plastic or other material which is compatible with MRI and other diagnostic and testing procedures. For example, as shown in FIG. 3, one portion of the fastener members 13 and 14 is secured to the back portion 12 by means of a rivet 29, which is preferably made of nylon or like material. As shown in FIG. 8, rivets 29 extend through apertures 123 and 124 provided in the back portion 12. The front and back portions 11 and 12 are contoured and have preformed elongated slot patterns 21 and 22 respectively, to provide a predetermined flexing structure for forming the shell of the device 10 to the neck and head of a patient.

Figure 4:
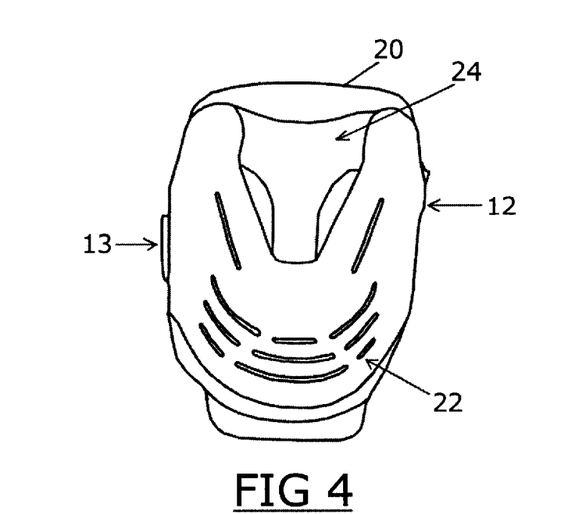
FIG. 4 is a plan view of the back portion of the cervical collar assembly.

Unlike prior art cervical collar devices which rely primarily on chin support to control lateral movement, the mandible controls 16 and 17 also eliminate the feeling of the chin being constricted or trapped. As shown in FIGS. 3 and 4 the cervical collar assembly 10 has a back portion 12 which as shown is of a two piece construction and is provided with an occipital support 24, which supports and contours to the patient's head and neck. The occipital support 24 is shown attached to a main body of the back portion 12. The occipital support 24 is also made of a semi-rigid plastic material, which is MRI and biocompatible. The occipital support 24 resembles the shape of a "T" and mimics a human hand holding the back of the head using the thumb and forefinger. The upper portion of the back piece 24 "cradles" the occipital region, restricting movement in all three planes. As shown in FIGS. 1–4, the cervical collar device 10 also has pre-cut slots and slot patterns in the front and back portions 11 and 12. The slots provide a lightweight and malleable structure to provide greater conformity to the anatomy of a patient. These slots also provide better air circulation through the device to produce a breathable collar structure for extended wear.

Figure 6:
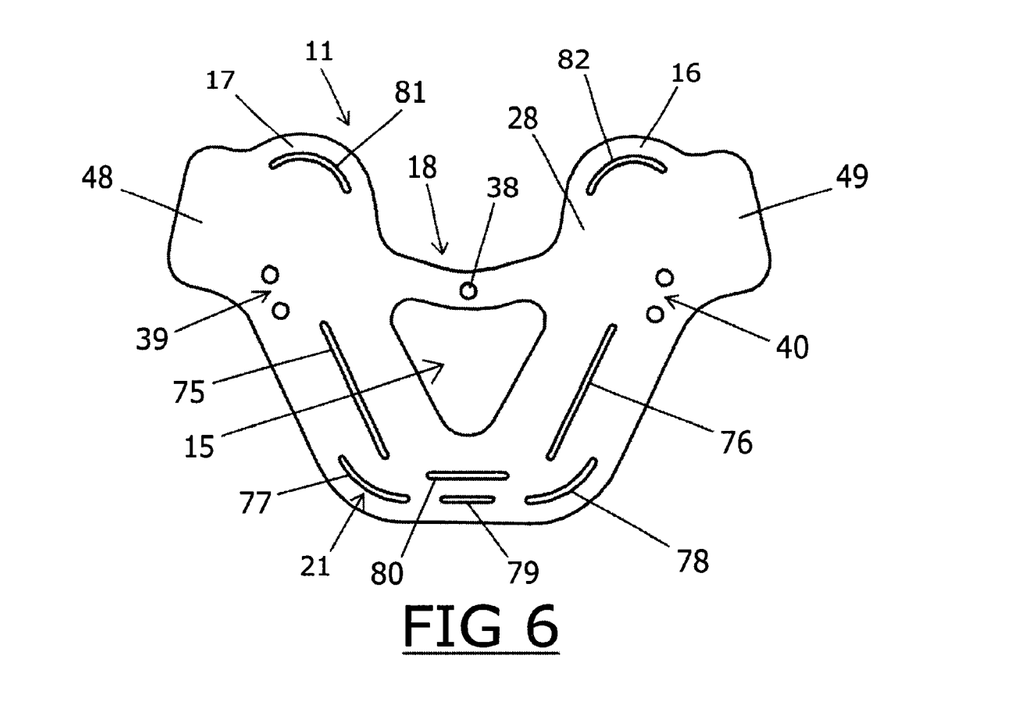
FIG. 6 is a plan view of the front portion of the cervical collar assembly of FIG. 1.

As shown in FIG. 6, the front portion 11 is shown to have upwardly extending wings or tabs 16 and 17 which are mandible control members to control the tilt or lateral movement of the patient's head by engaging the opposing lower jaw areas. As further shown, the front portion 11 is shown comprised of a body member 28 having upwardly extending wings or mandible control members 16 and 17, one on either side of central opening 18. End tabs 48 and 49 are shown on opposite sides of the body 28 and an opening 15 is shown centrally disposed in the body member 28. The opening 15 is provided for the trachea of a user. A pattern of a plurality of elongated slits 21 are shown extending through body member 28.

As shown in FIG. 6, the body member 28 of front portion 11 is shown in a flat, non-conforming state. The body member 28 is shown to have a plurality of elongated slots which are provided to permit the body member 28 to be bent and conformed to the front of the user's neck and head. Specifically, curved top slots 81 and 82 are shown in the mandible control wings 16 and 17 and curved bottom slots 77 and 78 are shown at the bottom sides of the body member 28. Centrally positioned at the bottom of the body member are slots 79 and 80 and spaced from the trachea opening 15 are slanted side slots 75 and 76. The cooperation of these slot patterns permit the front portion 11 of the shell to be formed, as shown in FIGS. 1 and 2. Further, the slots permit the transfer of air with the front foam pad member 19. Also shown in FIG. 6 are aperture 38 and apertures 39 and 40 which are provided for fastening the chin support member 23 to the inside of the front portion 11.

Figure 5:
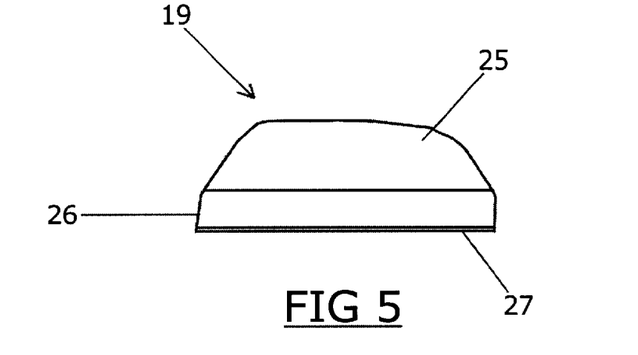
FIG. 5 is a plan view of the layered padding for the interior of the cervical collar assembly.
Figure 10:
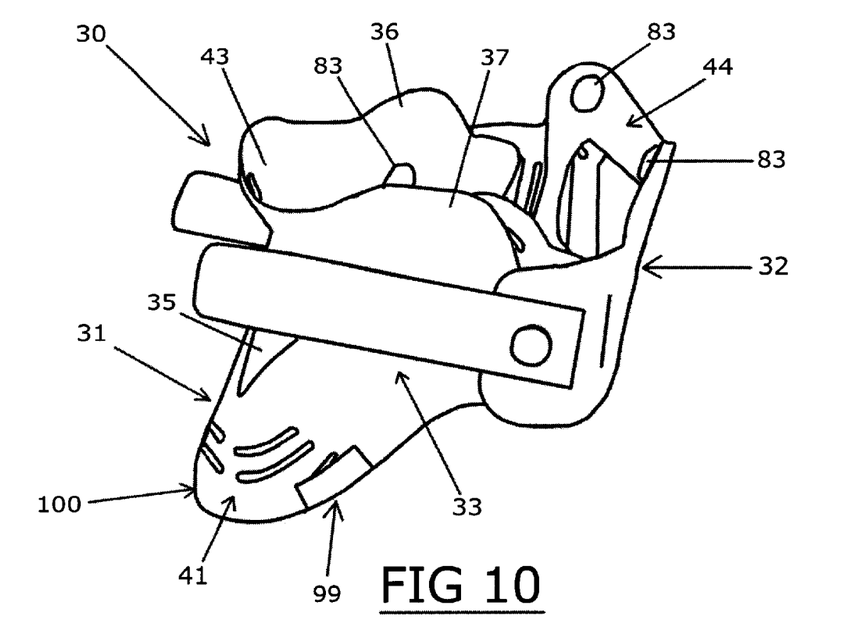
FIG. 10 is a perspective view of another embodiment of the cervical collar assembly of the present invention.
Figure 11:
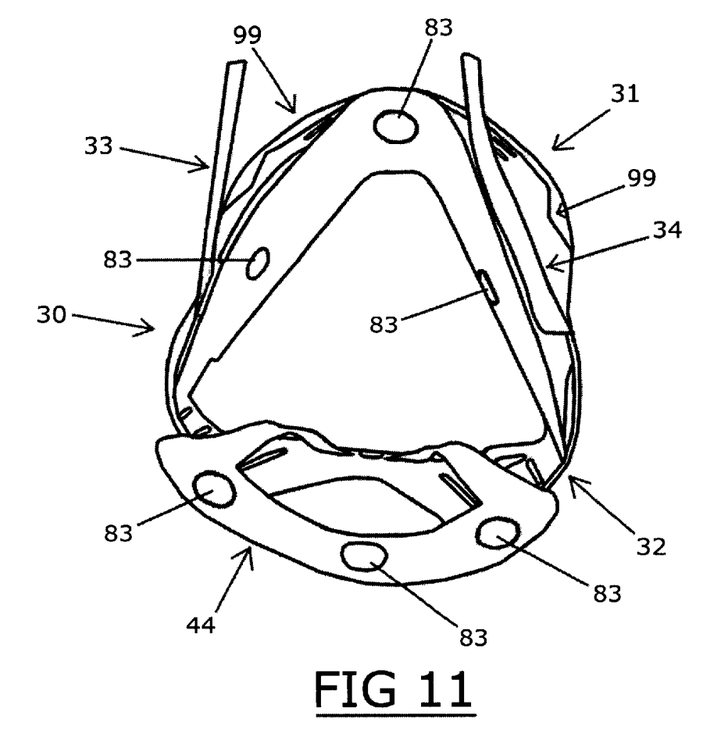
FIG. 11 is a top view of the cervical collar assembly of FIG. 10.

As shown in FIGS. 1 and 2, and particularly in FIG. 5, the cervical collar device 10 is shown to have a padding assembly comprising front and back laminated foam pad members 19 and 20. The foam pad members have a laminated structure comprising a fabric layer 25, a foam layer 26 and a skin contact fabric layer 27. The foam layer 26 is preferably of an open cell foam construction, such as 4 lb. polyurethane ester foam or the like. The open cell foam layer 26 permits moisture to be carried from the skin contact layer 27 to the outside of the shell. The foam pad members 19 and 20 are preferably removable from the front and back portions 11 and 12. The skin contact layer 27 is constructed of a moisture wicking material, which is preferably washable. Pad member 19 is shown attached to the front portion 11 and pad member 20 is shown attached to the back portion 12. As shown, the pad members 19 and 20 extend beyond the upper and lower peripheries of the front and back portions 11 and 12. The laminated pad members 19 and 20 each have a side or surface that attaches to the inside of the front and back portions 11 and 12 via a hook and catch fastening system, such as Velcro, for example. Thus, a fabric layer 25, such as a washable cotton loop fabric, is provided for connection to the hook portion of the fastening system used in connection with the shell structure. For example, fastening members 83 are shown in FIGS. 10 and 11 which permit the front and back foam pad members 19 and 20 to be secured to the front and back portions of the shell of embodiment 30. Embodiment 10 is similarly constructed. Further, a plurality of hook fastening pieces, i.e., five on each of the interiors of the front and back portions 11 and 12, may be provided on the interior of the shell.

The skin contact layer 27 of the laminated padding 19 is preferably of a breathable fabric construction which wicks away moisture, i.e., Cool-Max™ fabric provided by DuPont. The laminated padding members preferably have a uniform thickness, i.e. $3/8$–$1/2$ inches in thickness. The fabric layer 25 may be laminated onto one side of the foam layer 26 and the skin contact layer 27 may be adhesively fixed on the opposite side of the foam layer. Other lamination means known in the art may also be utilized, however. As shown, the foam pad members 19 and 20 extend above and below the shell structure.

The front and back portions 11 and 12, the chin support member 23 and the rear support member 24 are preferably constructed of a semi-rigid formed plastic material, i.e. polyethylene (LDPE or HDPE) or the like. The formed plastic front and back portions 11 and 12 may have a thickness of approximately $1/16$–$3/32$ inches and has a plurality of slots formed in the front portion 11 and a plurality of slots in the back portion 12. The respective slots provide a lighter weight device, which provides a conforming fit to the user and which provides air circulation to the body of the wearer. The chin support member 23 may have a thickness of approximately 0.040 inches and the rear support member 24 may have a thickness of approximately 3/32 inches.

Figure 7:
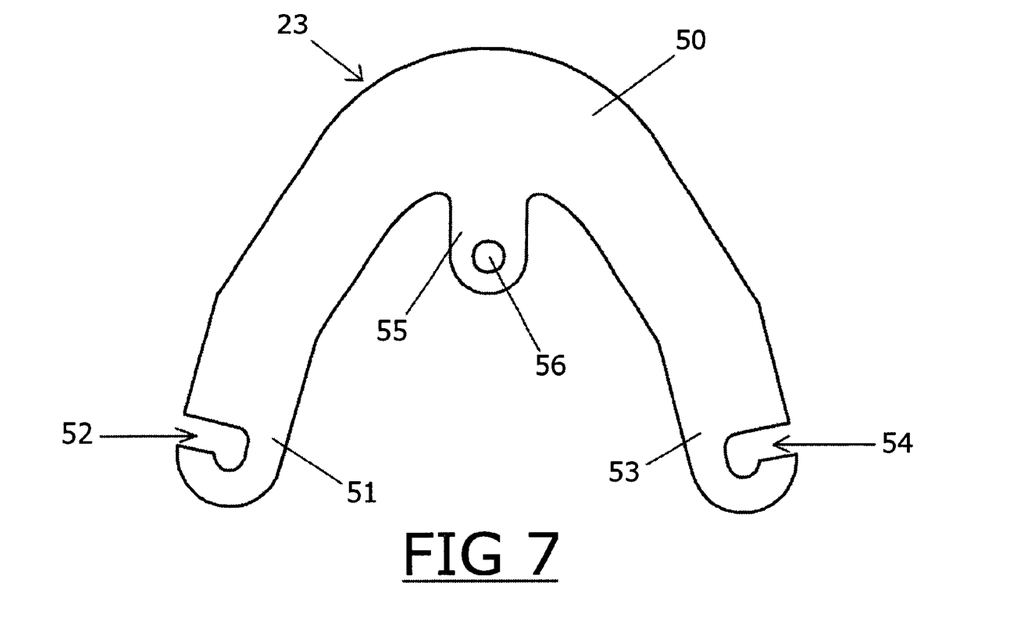
FIG. 7 is a plan view of the chin support member attaching to the front portion of FIG. 6.

As shown in FIGS. 1 and 2, and in FIG. 7, the C-shaped chin support member 23 adjustably connects at its ends 51 and 53 to the interior of the front portion 11 although the support 23 may be permanently secured. For example, a plurality of rivets, i.e., nylon fluted snap rivets, may be positioned on the interior surface of the front portion 11 to adjustably receive the notched fastening ends of the chin support member 23. Specifically, slots 52 and 54 are provided so that the chin support member 23 may be attached to the inside of the body member 28 of the front portion 11. This adjustment permits the chin support to be secured at a desired angle. A central tab 55 with aperture 56 is shown centrally positioned for connection to the front portion 11.

Figure 9:
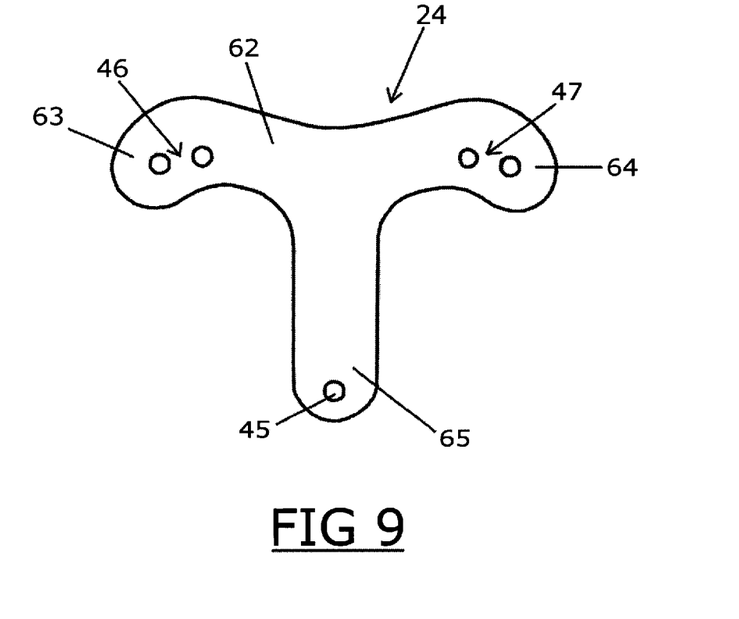
FIG. 9 is a plan view of the T-shaped rear occipital support member that attaches to the back portion of FIG. 8.

As shown in FIG. 9 the T-shaped rear support member or occipital support member 24 is shown connected to the back portion 12 to support the occipital area or the lower back part of the head where it merges with the neck.

As shown in FIGS. 8 and 9, the rear portion 12 and the occipital support member 24 are there shown. The rear portion 12 is further shown in FIGS. 3 and 4. The rear portion 12 is comprised of a body member 57 having end tabs 58 and 59 and upper tabs 60 and 61. A central, generally V-shaped opening is shown between the upper tabs 60 and 61. A plurality of elongated openings or slits 22 are shown extending through the body member 57 and which are provided to permit the body member 57 to be formed about the neck of a user. The body member 57 of back portion 12 is shown in a flat, non-conforming state. The body member 57 is shown to have a plurality of elongated slots which are provided to permit the body member 57 to be bent in a conforming state to the rear of the user's neck and head. Specifically, angled side slots 84 and 85 are shown spaced from the V-shaped central opening. Further, end slots 88 and 89 and end slots 86 and 87 are shown positioned adjacent end tabs 59 and 58, respectively. Centrally positioned at the bottom are curved slots 96, 97 and 98. Curved slots 93, 94, 95 and 90, 91 and 92 are shown spaced from the bottom slot pattern. The individual slots of the slot patterns are shown to be spacially parallel and arranged whereby the cooperation of the slots and slot patterns permit the back portion 12 of the shell to be formed as shown in FIGS. 3 and 4. As previously discussed with respect to the front portion 11, the slots in the back portion 12 likewise permit the transfer of air with the back foam pad member 20. Further, FIG. 8 shows aperture 120 and apertures 121 and 122 which are provided for fastening the rear support member 24 to the inside of the back portion 12.

FIG. 9 shows the occipital support member 24 which is positioned within the V-shaped opening of the body member 57. The member 24 is shown to have a body 62 having end tabs 63 and 64 and a bottom tab 65. Apertures 46 and 47 are shown in the end tabs 63 and 64 and aperture 45 in the bottom tab 65. The apertures are used with fastening means to secure the occipital support member 24 to the inside of the back portion 12. The respective apertures are aligned and adapted to receive a fastening member, such as a rivet or similar fastener, however, other fastener means are within the purview of this invention.

FIGS. 10 and 11 show another embodiment of the cervical collar assembly of the invention. The assembly 30 is shown to have a shell member comprised of a front portion 31, a back portion 32 and a fastening structure to adjustably secure the front and back portions 31 and 32. Hook and catch fastener 33 and 34 are shown. The latter fasteners extend on the outside and between the front and back portions 31 and 32 to provide an adjustable shell member. The front portion 31 is shown to have a trachea opening 35 and upwardly extending mandible control wing members 36 and 37. Chin support member 43 is shown positioned at the top and front of the front portion 31. The chin support member 31 may be secured or adjustably secured to the inside of the front portion 31. Further, elongated slots in a pattern 41 is shown.

As further shown in FIG. 10, the cervical collar device 30 has a structural configuration to disperse and cushion the weight of the device 30 as well as the resultant head and neck forces of the patient on the device 30. It has been found that a concentrated pressure over time to the patient's body can result in skin breakdown, i.e., ulcerated skin. The weight on a chin support by the chin and neck may result in those detrimental concentrated forces as may the head force on the occipital contact area. Thus, the chin support 43 and the occipital support 44 are designed to spread those forces to provide stability and to minimize pressure points. Further, the bottom 100 of the front portion 31 has a generally flat and rounded edge configuration to spread the weight across the sternum or chest areas of the wearer. Further, the front portion 31 is shown to have a gasket member 100 to further cushion the device 30 against the patient's body. The rounded and flat contours are also provided on the back portion 32 of the device 30 and is also shown with respect to the front and back portions 11 and 12 of device 10. The gasket member 99 is preferably constructed of rubber or a foam which is wrapped and glued, for example, around the device elements which contact the patient's body areas. For example, the mandible control members 36 and 37 and the upper part of the chin support 43 may be similarly cushioned. The corresponding elements of the cervical collar device 10 may also be provided with such gasket members 99.

Figure 12:
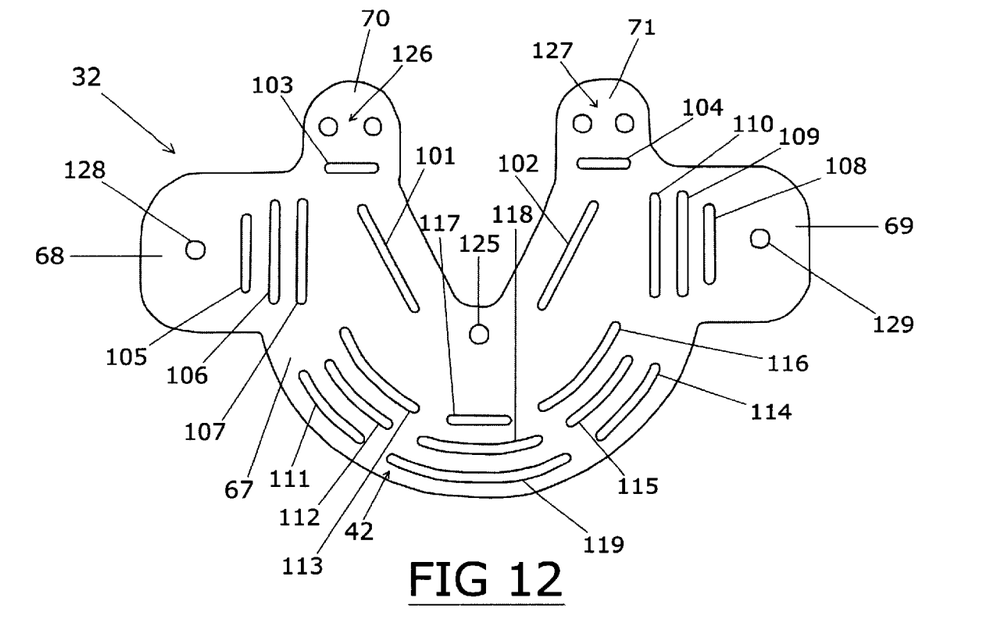
FIG. 12 is a plan view of the back portion of the cervical collar assembly of FIG. 10.
Figure 13:
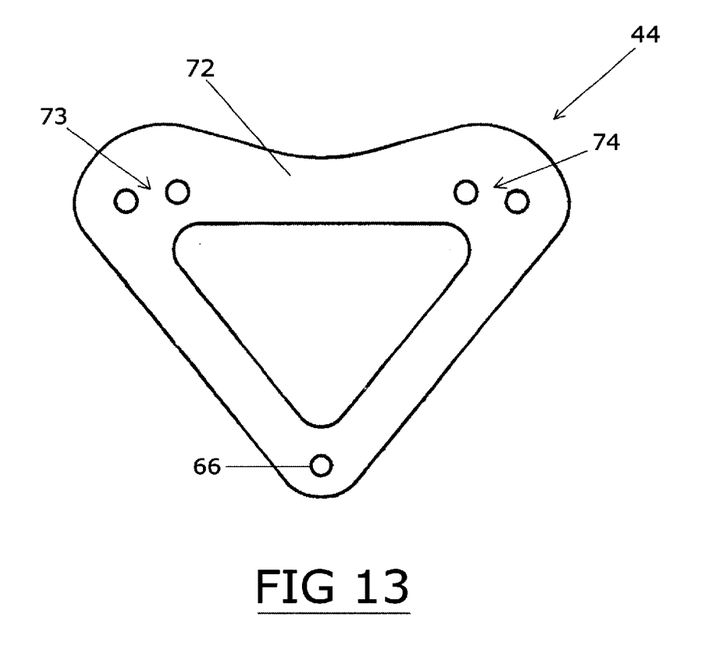
FIG. 13 is a plan view of the triangular occipital support member attached to the back portion of FIG. 12.

As further shown in FIGS. 12 and 13, the back portion 32 and the occipital support member 44 are different from those shown with respect to the assembly 10. Specifically, the support member 44 is shown to have a triangular shaped body 72 having an interior opening designed to prevent any scar tissue from being touched when the assembly 30 is worn by a user.

The back portion 32 is shown to have a body member 67 having upper tab members 70 and 71, respectively. Centrally positioned is a V-shaped opening extending downward from the upper tabs and wherein the triangular support 44 is fastened to the interior side of the body 67. Elongated slot pattern 42 is shown in back portion 32 as will be further described. End tabs 68 and 69 are shown extending outward and having slots 105, 106, 107 and 108, 109, 110 respectively. A centrally positioned aperture 125 is shown as well as angled slots 101 and 102. At the bottom and bottom sides of the body 67 are centrally positioned slots 117, 118, 119 and aligned slots 111, 112, 113 and 114, 115, 116 are shown positioned upwardly therefrom. Elongated slots 103 and 104 are shown positioned below upper tabs 70 and 71. The purpose of the slots and slot patterns and the apertures are generally the same as those described with respect to the assembly 10.

Referring to FIGS. 12 and 13, the triangular occipital support member 44 has an aperture 66 which aligns with aperture 125 of the back portion 32 for fastening purposes, i.e., by means of a rivet. Apertures 73 and 74 align with apertures 126 and 127 of the back portion 32 and may be similarly fastened. Apertures 128 and 129 of the back portion 32 are provided for connection of the fastening structures 33 and 34, which are provided to adjustably connect the back portion 32 to the front portion 31 of the shell structure.

In use, the front portion 11 of the cervical collar device 10 is held in place while back portion 12 is applied to the back of a patient's head such that the occipital support 18 is resting under the occipital region of the patient's head. The sides of the back portion 12 are placed over the sides of the front portion 11 and the hook fastener straps 13, 14 are then applied to the loop fastener material on the front portion 11.

As many changes are possible to the embodiments of this invention, utilizing the teachings thereof, the description above and the accompanying drawings should be interpreted in the illustrative and not the limited sense.

That which is claimed is:

1. A cervical collar assembly to immobilize the neck and head of a user, comprising:
   a) an adjustable and conformable shell member having a front member having a center opening and opposing tab members extending upwardly therefrom, a back member having a center opening, said shell member having means to adjustably join said front and back members, said front member and said back member having a rounded configuration on the top thereof and wherein said front and back members have gasket members on edges thereof;
   b) a chin support member positioned in said center opening of said front member, said chin support member having means to secure said chin support member to said front member;
   c) an occipital support member positioned in said center opening of said back member, said occipital support member having means to secure said occipital member to said back member; and
   d) a pad member secured within said conformable shell member, said shell member having means to secure said pad member to said front member and said back member.

2. The cervical collar assembly of claim 1 wherein said front member and said back member each have a plurality of elongated slits extending therethrough for conforming said shell about the neck and head of a user.

3. The cervical collar assembly of claim 2 wherein said front member has a predetermined pattern of slits therethrough and wherein said back member has a predetermined pattern of slits therethrough, said predetermined pattern of slits including a plurality of slits on opposing sides of said front member and said back member.

4. The cervical collar assembly of claim 1 wherein said cervical collar is constructed of MRI and biocompatible materials.

5. The cervical collar assembly of claim 1 wherein said pad member includes an open cell foam material.

6. The cervical collar assembly of claim 1 wherein said fastening means is comprised of a hook and loop fastening structure.

7. The cervical collar assembly of claim 1 wherein said chin support member includes adjustable securement means for attaching said chin support member to said front member.

8. The cervical collar assembly of claim 1 wherein said occipital support member is a T-shaped member or a triangular member.

9. The cervical collar assembly of claim 1 wherein said pad member extends outward from above and below said front member and said back member of said shell member.

10. A cervical collar assembly to partially immobilize a user's head and neck comprising:
    a) a semi-rigid front portion having opposing side mandible control tabs for restricting lateral and rotational head and neck movement of a user and having a bottom edge contoured for resting upon the sternum and trapezius of the user;
    b) a semi-rigid, adjustable chin support member having attachment means at each end for the adjustable attachment to said front portion;
    c) a semi-rigid back portion being contoured to conform and to support the neck and the sides of the back of the head of a user, said back portion further having a top edge having an occipital opening; and
    d) a semi-rigid occipital support member for restricting head and neck movement and being contoured to conform and to support the neck, occipit, and sides of the back of the head, said occipital support member being positioned in said occipital opening of said back portion and attached to said back portion, said occipital support member having a triangular-shaped configuration.

11. The cervical collar assembly of claim 10, wherein said cervical collar assembly includes a laminated, open cell foam pad member.

12. The cervical collar assembly of claim 11, wherein said pad member is breathable, moisture wicking, and washable.

13. The cervical collar assembly of claim 12, wherein said pad member has at least one hook and catch fastener for attachment to said cervical collar.

14. The cervical collar assembly of claim 10, wherein said occipital support member has a generally T-shaped configuration.

15. The cervical collar assembly of claim 10, wherein said front and back portions of the cervical collar assembly have a plurality of slits therein for flexion conformance and air circulation.

16. The cervical collar assembly of claim 10, wherein said front portion has an aperture therethrough for exposing the user's trachea.

17. The cervical collar assembly of claim 10, wherein the front and back portions are joined for adjustment to each other using at least one hook and catch fastener.

18. The cervical collar assembly of claim 10, wherein said front portion, back portion, chin support, and said occipital support are constructed of a rigid thermoformed plastic material.

19. A cervical collar assembly to partially immobilize a user's head and neck, said assembly comprising:
    a) an adjustable shell collar structure further comprising a semi-rigid front portion having opposing side mandible control tabs for restricting lateral and rotational head movement of a user and a semi-rigid back portion being contoured to conform to and to support the neck and the sides of the back of the head of the user, said back portion having a top edge having an occipital opening, and said front portion and said back portion having a plurality of elongated and aligned slots for forming the assembly to the neck and head of a patient, said front and bottom portions each having a bottom edge and said elongated slots being aligned in an arrangement along and adjacent and generally parallel to said bottom edges of said front and back portions of said shell collar structure;
    b) a padding structure attached to said adjustable shell collar structure;

c) a semi-rigid, chin support member having attachment means at each end for the attachment to said front portion; and d) a semi-rigid occipital support member for restricting head and neck movement and being contoured to conform to and to support the neck, occiput, and sides of the back of the head, said occipital support member being positioned in said occipital opening of said back portion and attached to said back portion.

20. The cervical collar assembly of claim 19, wherein said occipital support member has a generally T-shaped configuration.

21. The cervical collar assembly of claim 19, wherein said occipital support member has a triangular-shaped configuration for reducing pressure on any scar tissue present on the back of the neck of the user.

22. A cervical collar assembly of claim 19, wherein said padding structure is constructed of laminated, open cell foam layer and a breathable, moisture wicking, and washable layer.

23. The cervical collar assembly of claim 19, wherein said front portion, back portion, and chin support member are constructed of a rigid, biocompatible plastic material.

24. The cervical collar assembly of claim 19, wherein said chin support member is adjustable and wherein said front portion has an interior having a plurality of rivets and said adjustable attachment means of said chin support is comprised of a notch on each end of said chin support to hook onto two said rivets.

25. The cervical collar assembly of claim 19, wherein said plurality of elongated and aligned slots include at least one elongated slot disposed at the center along said bottom edges of said front and back portion of shell collar structure.

26. The cervical collar assembly of claim 19, wherein said plurality of elongated and aligned slots include at least one arrangement of two parallel slots spaced from said bottom edges of said front and back portions of said shell collar structure.

* * * * *